(12) United States Patent
Gaida

(10) Patent No.: US 7,699,468 B2
(45) Date of Patent: Apr. 20, 2010

(54) OPHTHALMOLOGIC SURGICAL MICROSCOPE HAVING A MEASURING UNIT

(75) Inventor: Gerhard Gaida, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 0 days.

(21) Appl. No.: 12/073,591

(22) Filed: Mar. 7, 2008

(65) Prior Publication Data

US 2008/0198329 A1 Aug. 21, 2008

Related U.S. Application Data

(63) Continuation-in-part of application No. PCT/EP2006/008616, filed on Sep. 5, 2006.

(30) Foreign Application Priority Data

Sep. 7, 2005 (DE) .................. 10 2005 042 436

(51) Int. Cl.
*A61B 3/10* (2006.01)
*A61B 3/14* (2006.01)

(52) U.S. Cl. ...................... 351/205; 351/206

(58) Field of Classification Search ......... 351/205–208; D16/222; 352/5, 62; 359/36, 376, 462–477
See application file for complete search history.

(56) References Cited

U.S. PATENT DOCUMENTS

| 3,791,719 | A | * | 2/1974 | Kratzer et al. ............... 351/211 |
| 5,493,109 | A | | 2/1996 | Wei et al. |
| 5,828,439 | A | | 10/1998 | Ueno |
| 6,004,314 | A | | 12/1999 | Wei et al. |
| 6,550,917 | B1 | | 4/2003 | Neal et al. |
| 2002/0115988 | A1 | | 8/2002 | Holladay |
| 2003/0139736 | A1 | | 7/2003 | Sander |
| 2004/0246440 | A1 | | 12/2004 | Andino et al. |
| 2005/0007551 | A1 | | 1/2005 | Wakil et al. |
| 2005/0024585 | A1 | * | 2/2005 | Dai ............................ 351/205 |
| 2005/0203422 | A1 | * | 9/2005 | Wei ............................ 600/476 |

FOREIGN PATENT DOCUMENTS

| DE | 42 07 630 | 9/1993 |
| DE | 43 10 561 | 9/1994 |
| EP | 0 247 260 | 12/1987 |
| WO | WO 03/030763 | 4/2003 |
| WO | WO 2004/003468 | 1/2004 |

OTHER PUBLICATIONS

German Office Action Aug. 2006.
Holladay, "Refractive Power Calculations for Intraocular Lenses in the Phakic Eye", American Journal of Ophthalmology, vol. 116, 1993, pp. 63 to 66.
"Durchschnittsauge von Gullstrand", ABC der Optik, Verlag Werner Dausien, Hanau/Main, 1961, pp. 83 to 85.
Hee et al, "Optical Coherence Tomography of the Human Retina", Arch Ophthalmol., vol. 113, Mar. 1995, pp. 325 to 332).

* cited by examiner

*Primary Examiner*—Jessica T Stultz
*Assistant Examiner*—Mahidere S Sahle
(74) *Attorney, Agent, or Firm*—Walter Ottesen

(57) ABSTRACT

A surgical microscope (100) for ophthalmology includes a measuring unit (110) for determining at least one characteristic value of a patient eye (104). The measuring unit (110) is connected to a computer unit (120) which calculates a model of the patient eye (104) based on the determined characteristic variables. The surgical microscope also includes a display device for displaying the calculated model of the patient eye (104) or characteristic variables that are derived from the calculated model.

15 Claims, 3 Drawing Sheets

OPHTHALMOLOGIC SURGICAL MICROSCOPE HAVING A MEASURING UNIT

CROSS REFERENCE TO RELATED APPLICATIONS

This application is a continuation-in-part application of international patent application PCT/EP 2006/008616, filed Sep. 5, 2006, designating the United States and claiming priority from German application 10 2005 042 436.8, filed Sep. 7, 2005, and the entire content of both applications is incorporated herein by reference.

FIELD OF THE INVENTION

The invention relates to a surgical microscope for ophthalmology having a measuring unit for determining at least one optical characteristic variable of the eye of a patient.

BACKGROUND OF THE INVENTION

The geometric length between optically effective surfaces of the eye is understood to be included in the optical characteristic variables of an eye of a patient whereat a jump or a non-vanishing gradient of the index of refraction occurs or whereat an absorption of light takes place. The local radii of the surfaces, that is, their Gaussian curvatures can, however, likewise be considered as optical characteristic variables of an eye of a patient. An optical characteristic variable of a patient eye is, inter alia, also the refractive index or the refractive power of an optically effective component thereof.

A surgical microscope of the kind referred to above is disclosed in U.S. Pat. No. 6,004,314. Here, a surgical microscope is described having a coherence interferometer in the form of an OCT measuring unit. This OCT measuring unit provides an OCT scanning beam which can be scanned in a transverse direction across the cornea of a patient eye to determine the thickness thereof and to measure the precise course of the forward surface of the cornea and the rearward surface thereof.

United States patent publication 2003/139736 A1 discloses an ophthalmologic surgical microscope having an integrated refractometer. With the aid of this refractometer, the optical characteristic of an artificial eye lens, which is placed during cataract surgery, can be monitored during the course of the surgical procedure so that it is possible to correct the artificial eye lens as required.

U.S. Pat. No. 5,828,439 discloses a refractometer with which the refractive power of the human eye can be determined during a surgical procedure. A measuring unit is integrated into this refractometer for measuring a non-optical characteristic variable of the eye in the form of the inner pressure of eye. This inner pressure is used to correct a measured refractive power value.

German patent publication 4,310,561 discloses an arrangement for determining refraction and visual acuity during a surgical procedure on the human eye. This arrangement permits imaging a test card on the retina of the eye of the patient which is illuminated by means of a light source and which is suitable for measuring an imaging sharpness of the eye. When the physician detects with the arrangement a sharp test card image on the retina of the patient eye, then an absolute refraction value for the eye being examined can be determined from the apparatus parameters of the arrangement. The device is combined with a surgical microscope and, in turn, permits a physician to make a refraction determination during the course of a surgical procedure when viewing the eye of the patient.

An arrangement for analyzing and correcting the refractive power of a human eye is described in European patent publication 0,247,260. The arrangement includes a data store wherein data of an idealized patient eye are stored for the following: different axial eye lengths; patient age; sex; and, also values for the inner pressure of the eye. In this arrangement, means are provided for determining the particular corneal topography. The arrangement further includes a laser unit with which incremental amounts of the cornea of the human eye can be removed. The removal is so adjusted that a desired topography of an idealized patient eye results. The development of cataract surgery to an ever more careful surgical technique accompanying refractive surgery of the cornea has led to an increase in the demands on the optical characteristic of the patient eye after cataract surgery. It is expected that the full visual acuity is achieved without correcting spectacles.

In addition, in ophthalmologic surgery, it is attempted to correct for reduced visual capacities of the human eye when the pupil width of the eye is greater than 2 mm. These visual deficiencies are caused by the geometric optical correction of the eye which is by nature inadequate. Here it is sought, for patients with average or below average vision, to assist these patients in obtaining an above average visual acuity (that is, >1) via intervention into the optical characteristics of the human eye. This above average visual acuity occurs only in exceptional cases in humans.

Finally, in ophthalmologic surgery, efforts are being made to reverse the reduction of the accommodative power of the human eye because of age which is the so-called presbyopia. Since the effectors of the accommodation are the so-called ciliary muscles, there is a way to improve the accommodative power of the eye in older persons in that the aging natural lens of the eye is exchanged for an artificial lens.

With this as background, it is desirable and necessary for ophthalmologic surgery that the refractive state of a patient eye after surgery can be predicted as precisely as possible, especially the state in the eye interior and the state of the eye lens. For such a prediction, precise optical measurement methods are known and can, for example, be carried out with the IOL Master of Carl Zeiss Meditec AG in the context of a preoperative characterization of the eye.

However, in the present state of cataract surgery, only an intraocular lens is inserted which is selected based on preoperative data. The healing of the wound of the eye is then awaited during which the optical characteristic variables often change such as the distance of the refractive components of the eye. Only after the completion of the healing of the wound do the optical characteristics of the eye stabilize.

In the context of this background, it is desirable to control the optical characteristics of the eye also during surgery to be able to rapidly recognize an unwanted deviation from the preplanned state so that the surgery can be modified as required. Furthermore, there are now surgical techniques (for example, injectionable intraocular lenses) which make it necessary to compensate optical characteristics of the eye during a surgical procedure. Up to now, it is only known in the state of the art to intraoperatively measure a single optical variable of the eye, for example, the refractive power thereof. However, the optical state of the eye cannot be reliably determined on the basis of this single optical characteristic variable. It has been shown that, in the course of a healing process after a surgical procedure on the eye, not only a single optically effective variable changes but a modification of several optical characteristic variables of the eye takes place whose optical effect possibly partially amplifies but also mutually weakens.

The human eye is an optical system which, as a rule, is far from perfect. In a perfect eye, which is also characterized as an emmetropic eye, light rays, which originate from a point in an object region, converge in the eye interior at a point which lies on the retina of the eye. However, in reality, this state never occurs. On the one hand, this is caused by the fact that an optical system, which has a limited aperture, images a mathematical point (whose diameter is zero), because of the diffraction of light, on a point whose diameter is greater than zero. On the other hand, this is caused by the situation that the optical components of the eye, namely cornea and lens, are far from perfect. When the curvature of the cornea is too great or the eye is too long, then the image of the object lies in a plane which is forward of the retina. This leads to the situation that the object is observed by the eye as being blurred. The corresponding vision defect is known as myopia. For the opposite situation, when the cornea is too flat or the eye is too short, the image, which is imaged by the eye, lies behind the surface of the retina. Again, an observed object appears blurred. This vision defect is known as hyperopia. Finally, a third vision defect is called astigmatism and this is caused by the optical areas in the eye having a certain elasticity. This elasticity has the consequence that, with the human eye, it is not at all possible to image a point precisely as a point. Rather, the best possible image of a point that the eye can generate is an ellipse.

Ophthalmologists and opticians know the vision defects listed. They can correct these vision defects with the aid of spectacles and contact lenses. It is also possible to undertake a vision defect correction with a surgical procedure on the eye, for example, by inserting a phakatic intraocular lens in the eye or via the so-called photo-refractive keratomileusis (PRK).

To improve an operative correction of visual defects, it is desirable to detect the condition of the eye during a surgical procedure thereon before, during and after a surgical procedure. Up to now, for example, in cataract surgery, an intraocular lens is inserted into the patient and the form of this lens is determined from preoperatively obtained patient data. In surgery, the optical characteristics of the eye on which surgery is performed cannot be monitored. This is problematic because, during the course of surgery, and during a healing of the wound, optical characteristic variables of the eye can change such as distances of refractive elements.

When it is possible to control the optical characteristics of the eye also during a surgical procedure, an unwanted deviation from a preplanned state can be rapidly detected and adapted or modified during the surgical procedure. In surgical procedures for reestablishing the accommodation while utilizing injectionable intraocular lenses, a compensation of the optical character of intraocular lenses and patient eyes are indeed necessary.

SUMMARY OF THE INVENTION

It is an object of the invention to provide a surgical microscope which, during an ongoing surgical procedure, quasi in real time, the optical state of a patient eye being operated upon can be reliably and completely determined.

This object is realized with the surgical microscope of the type described wherein the measuring unit is connected to a computer unit which computes a model for the patient eye based on specific optical characteristic variables and wherein a display device is provided for displaying the computed model of the patient eye or for displaying one or more characteristic variables of the patient eye derived from the computed model.

A model of a patient eye is understood to be an arrangement of optically effective surfaces and media in front of an image surface which simulates the retina. An imaging beam path, which is present there, corresponds at least approximately to the structural conditions in the human eye. One such model of a patient eye can, for example, be based on the "average eye of Gullstrand" which is described in the text entitled "ABC der Optik", published by Werner Dausien, Hanau/Main 1961, pages 83 to 85. Here, the optically effective surfaces are given for an exact eye model and a simplified eye model. The curvature of these surfaces and the distance as well as the index of refraction of the optical elements is also given for which an imaging beam path corresponds in good approximation to the natural structural conditions in an average healthy person having emmetropic eyes. In that, for an exact eye model according to Gullstrand or the simplified eye model, distances or curvatures are not pregiven but are understood as free parameters adapted to a specific patient eye, it is possible to describe a real patient eye with such a model.

The characteristic variables, which are derived from the computed model, are the dimensions of the vitreous body in the corresponding model, the eye length, the diameter of the eye lens in the model and/or the total refractive power of the patient eye.

In the area of optical design, it is known, with pregiven parameters of specific optical elements of an arrangement and with pregiven requirements (for example, the position of the image plane) to compute free parameters, that is, not previously determined parameters, by means of computer programs. On this basis, it is, for example, suggested in "American Journal of opthalmology", Vol. 116, pages 63 to 66 (1993) by Jack T. Holiday to determine the refractive power of intraocular lenses for a phakic patient eye.

An especially good model for a patient eye can be computed when the computation is based on two or more characteristic variables of the patient eye. Advantageously, these measured optical characteristic variables of the patient eye are those characteristic variables which possibly change the most during a surgical procedure and in the subsequent healing process. The measuring device is so configured that the device makes possible to obtain data for a complete characterization of the optical surfaces of the eye, especially the device makes possible the detection of aspheric surface forms and decenterings. In this way, the basis is provided, with a surgical intervention on the patient eye, to improve the vision capacity beyond normal vision capacity.

According to another feature of the invention, the measuring unit includes a coherence interferometer, for example, an OCT-system. The measuring device can, however, also be configured as a wave-front sensor. Likewise, the measuring unit can be configured as a refractometer, preferably, as a skiascope or as a keratometer. Also, a measuring unit for the travel-time measurement or a measuring unit having means for carrying out a light section method is suitable as a measuring unit in the surgical microscope. It is understood that also several measuring units can be provided in the surgical microscope. For example, a wave-front measuring unit having a skiascope and a refractometer can be combined in the surgical microscope. A computation of an especially reliable eye model is possible in that, in the surgical microscope, additional means for measuring non-optical characteristic variables of the patient eye are provided, for example, means for measuring the eye internal pressure.

The surgical microscope of the invention makes possible a display of a model and corresponding characteristic variables during the course of a surgical procedure. The measurement data for the model are determined during the course of surgery in order to be able to recognize an unwanted deviation from a planned state of the patient eye and to provide the surgeon with the capability to correspondingly change the surgical procedure as may be required thereby affording very substantial advantages for the patient.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
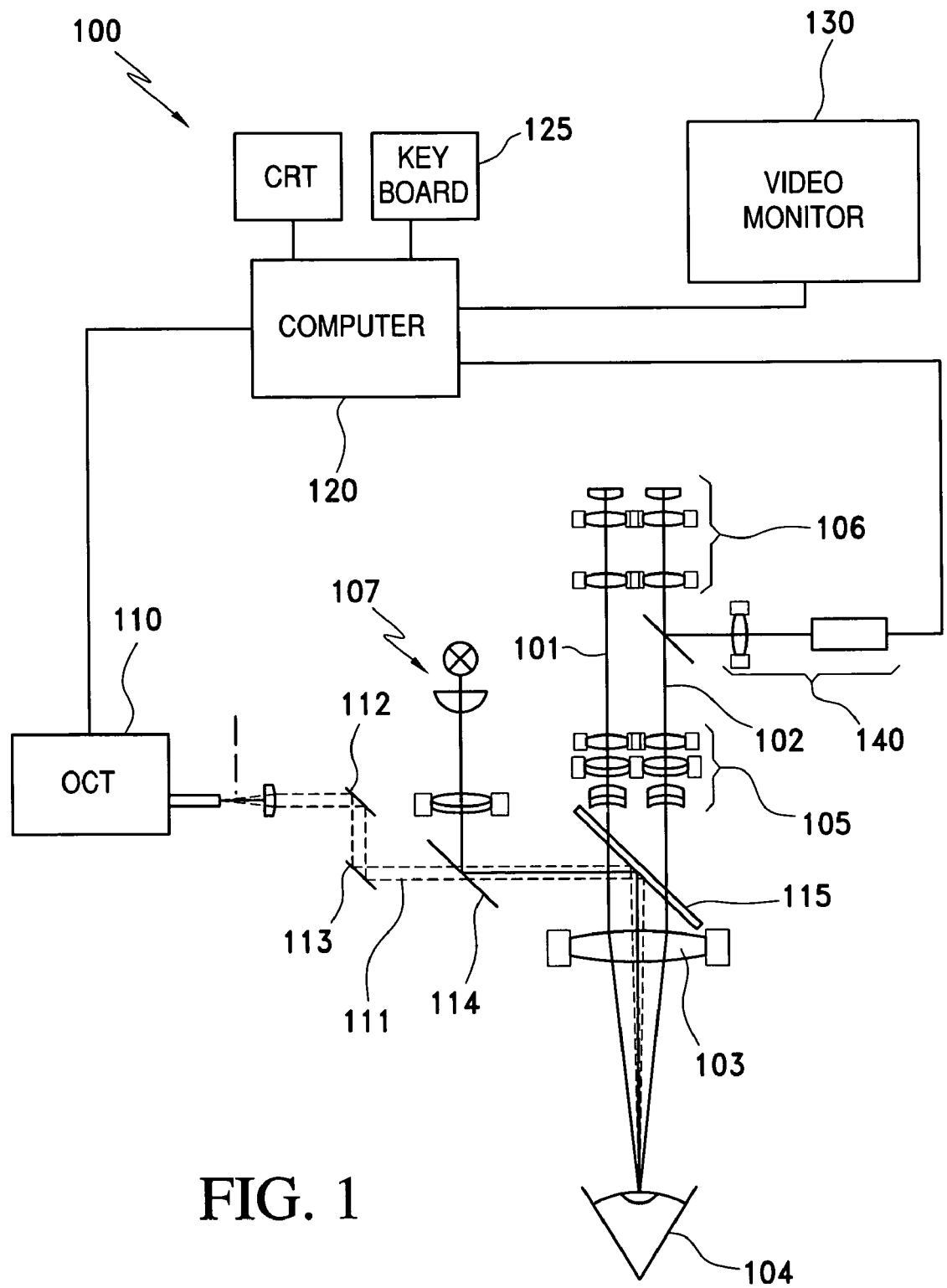
FIG. 1 is a schematic of a surgical microscope for ophthalmology for determining optical characteristic variables of a patient eye.

The ophthalmologic surgical microscope 100 of FIG. 1 includes a stereoscopic illuminating beam path (101, 102) which makes possible the examination of a patient eye 104 through a microscope main objective 103. The ophthalmologic surgical microscope 100 further has a zoom system 105 and an ocular 106. The surgical microscope 100 includes an illuminating system 107 which makes available illuminating light for the patient eye 104 through the microscope main objective 103.

As a measuring device for determining optical characteristic variables of the patient eye 104, the ophthalmologic surgical microscope 100 has a coherence interferometer in the form of an OCT-system 110. The OCT-system 110 provides a scanning light beam 111 of short coherent light which is guided to the patient eye 104 via displaceable scan mirrors (112, 113) and beam splitters (114, 115) through the microscope main objective 103. The light of the scanning light beam 111, which is scattered at the patient eye, returns at least in part to the OCT-system 110 via the same light path. In the OCT-system 110, the traveling path of the scanning light is then compared to a reference path. In this way, the precise positions of the scattering centers in the patient eye (especially, the positions of optically effective surfaces) can be detected with an accuracy which corresponds to the coherence length of the short coherent light in the scanning light beam 111.

A computer unit 120 is assigned to the OCT-system 110. The computer unit 120 computes a model for the patient eye 104 from the optical characteristic variables of the patient eye 104 made available by the OCT-system 110. The computer unit 120 is connected to a monitor 130 and a data in-reflecting unit 140 for the surgical microscope 100. The form of the display of the computed model on the monitor 130 can be selected via a keypad 125 of the computer unit 120 or by means of the data in-reflecting unit 140. It is also possible to select the display of the model in the form of a graphic or as a numeral set or character set. It is also possible to display selectively on the monitor 130 one, two, three, four or more characteristic variables derived from the model.

Figure 2:
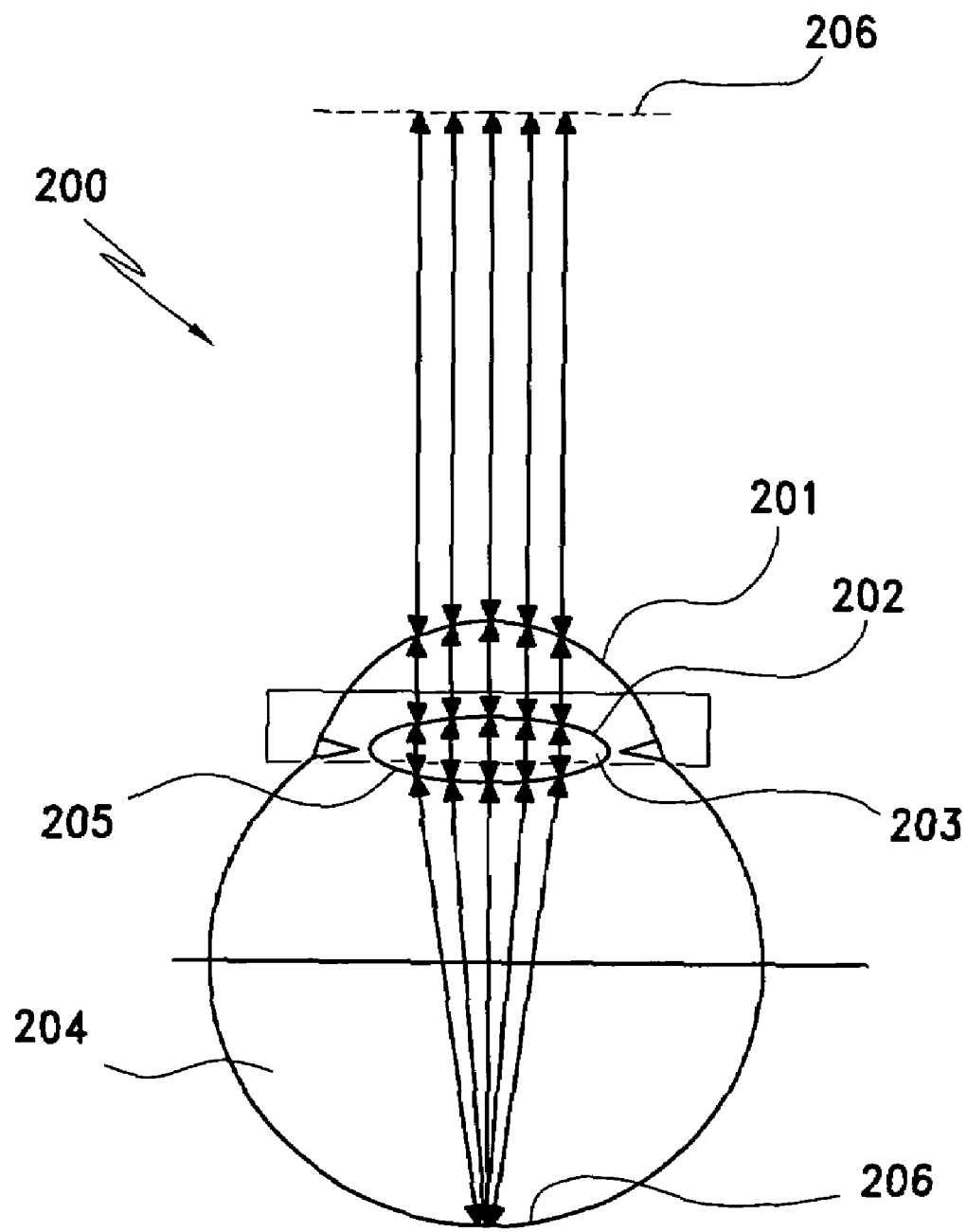
FIG. 2 is a model for a patient eye.

A model 200 for a patient eye is shown in FIG. 2. This model 200 is based on the simplified assumption that only three optically effective surfaces are present in a patient eye, namely, an outer surface 201 of the cornea, a surface 202 and a surface 205 of an eye lens 203 with the surface 202 facing toward the cornea and the surface 205 facing the vitreous body 204 of the eye.

With the OCT-system 110 of FIG. 1, it is possible to determine the exact course for discrete positions of the surfaces with respect to a reference plane 206. For this purpose, for example, the optical variable of the position and the optical variable of the precise course of the outer surface 201 of the cornea and the surface 202 of the eye lens facing the cornea can be measured and determined.

The model proceeds from the assumption of an eye adapted to infinity. This means that, in an emmetropic eye, light rays, which incident parallelly on the eye, are focused on the ocular fundus 206. From this constraint, there results a course which the surface 205 of the eye lens, which faces toward the vitreous body 204, has to have with a pregiven course of the outer surface 201 of the cornea and of the surface 202 of the eye lens 203 which faces toward the cornea.

This information is made available to a surgeon with the ophthalmologic surgical microscope shown in FIG. 1 during an ongoing surgical procedure. The surgeon is then in a position to correspondingly adapt an intraocular lens inserted into the eye.

Figure 3:
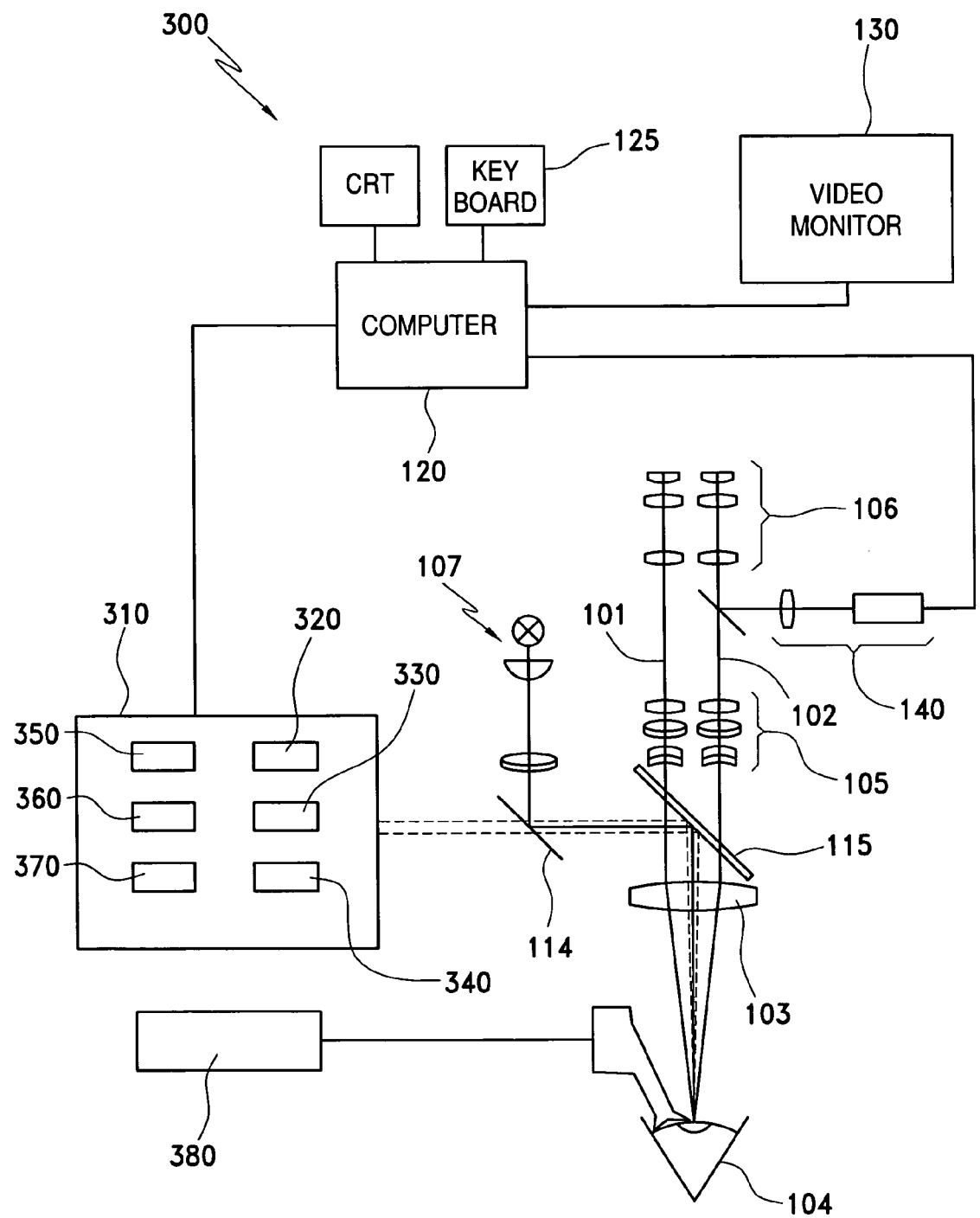
FIG. 3 is a schematic of a surgical microscope according to another embodiment of the invention.

In lieu of or in addition to the OCT-system, a refractometer, a skiascope or a keratometer can be integrated into the surgical microscope as shown in FIG. 3. Referring to FIG. 3, the surgical microscope 300 includes a measuring device 310 which includes a wave-front sensor 320. With a corresponding wave-front sensor 320 and a suitable illuminating beam, for example, the refractive power of the eye can be determined resolved as to location, that is, the refractive power of the eye can be measured distributed over the pupil of the eye at several locations. Preferably, such a location-resolved refractive power measurement can take place via the viewing beam path and the illuminating component beam paths in the surgical microscope 300. For a measurement of the distances of optically effective surfaces in the eye, these beam paths (that is, especially the beam paths via which the refractive power measurement takes place) can also be applied. Furthermore, it is possible in the surgical microscope to also provide units for measuring the non-optical characteristic variables of the eye such as a measuring unit for determining the inner pressure of the eye.

The measuring device 310 of the surgical microscope 300 of FIG. 3 further includes a refractometer 330, a skiascope 340, a keratometer 350, means 360 for measuring traveling time and means 370 for carrying out a light section method. In addition, surgical microscope 300 includes a device for measuring non-optical characteristic variables of the patient eye in the form of a measuring device 380 for measuring the internal pressure in the patient eye.

It is understood that the foregoing description is that of the preferred embodiments of the invention and that various changes and modifications may be made thereto without departing from the spirit and scope of the invention as defined in the appended claims.

What is claimed is:

1. An opthalmologic surgical microscope for use by a surgeon during an ongoing surgical procedure on a patient eye to continuously determine the optical state of said patient eye, said patient eye having optically effective surfaces including a first surface of the eye lens facing toward the vitreous body of said eye, a second surface of said eye lens facing toward the cornea of said eye and a third surface defining the surface of said cornea; said first, second and third surfaces having predetermined courses with respect to each other; the opthalmologic surgical microscope comprising:

a measuring device for measuring at least one optical characteristic variable which incorporates data characterizing said optical surfaces of said patient eye;

a computer unit connected to said measuring device for receiving the measured optical characteristic variable;

said computer unit being adapted to continuously compute a model including said first, second and third surfaces of said patient eye from said measured optical characteristic variable during the course of said surgical procedure; and, a display device connected to said computer unit and being adapted to continuously display the computed model of said patient eye to permit the surgeon to detect changes in the condition of the eye during surgery to facilitate adaptation to said changes of an intraocular lens inserted into said patient eye during said ongoing surgical procedure.

2. The opthalmologic surgical microscope of claim 1, wherein said display device is adapted to display a plurality of characteristic variables derived from said model.

3. The opthalmologic surgical microscope of claim 1, wherein said measuring device includes a coherence interferometer.

4. The opthalmologic surgical microscope of claim 1, wherein said measuring device includes a wave-front sensor.

5. The opthalmologic surgical microscope of claim 1, wherein said measuring device includes a refractometer.

6. The opthalmologic surgical microscope of claim 1, wherein said measuring device includes a skiascope.

7. The opthalmologic surgical microscope of claim 1, wherein said measuring device includes a keratometer.

8. The opthalmologic surgical microscope of claim 1, wherein said measuring device includes means for measuring running time.

9. The opthalmologic surgical microscope of claim 1, wherein said measuring device includes means for carrying out a light sectioning process.

10. The opthalmologic surgical microscope of claim 9, further comprising means for measuring non-optical characteristic variables of a patient eye.

11. The opthalmologic surgical microscope of claim 10, wherein said means for measuring non-optical characteristic variables of the eye measures the inner pressure of the eye.

12. A method for operating a surgical microscope for use by a surgeon during an ongoing surgical procedure on a patient eye to continuously determine the optical state of said patient eye, said patient eye having optically effective surfaces including a first surface of the eye lens facing toward the vitreous body of said eye, a second surface of said eye lens facing toward the cornea of said eye and a third surface defining the surface of said cornea; said first, second and third surfaces having predetermined courses with respect to each other; said surgical microscope including a measuring device for measuring at least one optical characteristic variable which incorporates data characterizing said optical surfaces of said patient eye; a computer unit connected to said measuring device for receiving the measured optical characteristic variable; said computer unit being adapted to continuously compute a model including said first, second and third surfaces of the patient eye from said measured optical characteristic variable during the course of the surgical procedure; and, a display device connected to said computer unit and being adapted to continuously display said computed model of the patient eye or characteristic quantities of the patient eye derived from said model, the method comprising the steps of:

measuring said at least one optical characteristic variable which incorporates said data characterizing said optical surfaces of said patient eye;

supplying the measured optical characteristic variable to said computer unit;

continuously computing a model including said first, second and third surfaces in said computer unit of said patient eye from said measured optical characteristic variable during the course of said surgical procedure; and, with said display device, continuously displaying the computed model of said patient eye to permit the surgeon to detect changes in the condition of the eye during surgery to facilitate adaptation to said changes of an intraocular lens inserted into said patient eye during said ongoing surgical procedure.

13. The method of claim 12, wherein a plurality of said characteristic variables are derived from said computed model and displayed utilizing said display unit as a graphical illustration or numerical value.

14. A stereoscopic surgical microscope for use by a surgeon carrying out an opthalmologic surgical procedure on a patient eye to continuously determine the optical state of said patient eye, said patient eye having optically effective surfaces including a first surface of the eye lens facing toward the vitreous body of said eye, a second surface of said eye lens facing toward the cornea of said eye and a third surface defining the surface of said cornea; said first, second and third surfaces having predetermined courses with respect to each other; the surgical microscope comprising:

a measuring device for measuring at least one optical characteristic variable which incorporates data characterizing said optical surfaces of said patient eye;

a computer unit connected to said measuring device for receiving the measured optical characteristic variable;

said computer unit being adapted to continuously compute a model including said first, second and third surfaces of said patient eye from said measured optical characteristic variable during the course of said surgical procedure; and, a display device connected to said computer unit and being adapted to continuously display said computed model of said patient eye or one or several characteristic variables of the patient eye to permit the surgeon to detect unwanted changes in the condition of the eye during surgery to so provide the surgeon with the capability to correspondingly change the surgical procedure during the course thereof as may be required.

15. The stereoscopic surgical microscope of claim 14, wherein said one or more characteristic variables is derived from said computed model in the form of at least one of the following: eye length of said patient eye; diameter of the eye lens of said patient eye; position of the cornea, course of said surface of the cornea; course of said second surface of the eye lens facing toward the cornea; and, course of said first surface of said eye lens facing toward said vitreous body.

* * * * *